(12) United States Patent
Anderson et al.

(10) Patent No.: US 6,906,207 B2
(45) Date of Patent: Jun. 14, 2005

(54) POLYMER ADDITIVE COMPOSITIONS AND ARTICLES COMPRISING NOVEL FLUORINATED AND ALKYLATED ALDITOL DERIVATIVES

(75) Inventors: John D. Anderson, Moore, SC (US); Nathan A. Mehl, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 264 days.

(21) Appl. No.: 10/337,764

(22) Filed: Jan. 7, 2003

(65) Prior Publication Data

US 2003/0181552 A1 Sep. 25, 2003

Related U.S. Application Data

(60) Division of application No. 09/816,965, filed on Mar. 23, 2001, now abandoned, which is a continuation-in-part of application No. 09/653,735, filed on Sep. 1, 2000, now Pat. No. 6,300,525.

(51) Int. Cl.$^7$ .................. C07D 323/04; C08K 5/15; C07C 45/00
(52) U.S. Cl. .............. 549/364; 512/1; 512/2; 512/12; 512/14; 512/25; 524/108; 568/428; 568/435
(58) Field of Search ............ 549/364; 524/108; 512/1, 2, 12, 14, 25

(56) References Cited

U.S. PATENT DOCUMENTS

| | | | |
|---|---|---|---|
| 3,201,363 A | 8/1965 | Spurlin et al. ............. 260/30.4 |
| 3,207,736 A | 9/1965 | Wijga et al. ............... 260/93.7 |
| 3,234,233 A | 2/1966 | Bolger et al. .............. 260/326 |
| 3,320,267 A | 5/1967 | Poos et al. ................. 260/295 |
| 3,367,926 A | 2/1968 | Voeks et al. .............. 260/93.5 |
| 3,527,736 A | 9/1970 | Averink et al. ........... 260/78.4 |
| 3,721,682 A | 3/1973 | Murai et al. .............. 260/340.7 |
| 3,793,401 A | 2/1974 | Nield et al. ................ 260/876 |
| 3,829,450 A | 8/1974 | Schmerling et al. ..... 260/346.3 |
| 3,873,643 A | 3/1975 | Wu et al. .................... 260/878 |
| 3,882,194 A | 5/1975 | Krebaum et al. ........... 260/878 |
| 3,928,687 A | 12/1975 | Wada et al. ................ 428/461 |
| 3,933,779 A | 1/1976 | Baron et al. ............... 260/93.5 |
| 3,941,746 A | 3/1976 | Stephen ..................... 260/45.8 |
| 3,954,913 A | 5/1976 | Uebele et al. .............. 260/880 |
| 4,016,118 A | 4/1977 | Hamada et al. ............ 260/17.4 |
| 4,039,491 A | 8/1977 | Ikeda et al. ................. 260/875 |
| 4,134,895 A | 1/1979 | Roth et al. ................. 260/326 |
| 4,134,927 A | 1/1979 | Tomoshige et al. ........ 260/878 |
| 4,154,816 A | 5/1979 | Roehl et al. ................ 424/68 |
| 4,371,645 A | 2/1983 | Mahaffey, Jr. ............. 524/108 |
| 4,452,942 A | 6/1984 | Shida et al. ................ 525/74 |
| 4,476,184 A | 10/1984 | Lubowitz et al. .......... 428/288 |
| 4,503,219 A | 3/1985 | Reffert et al. .............. 528/481 |
| 4,518,582 A | 5/1985 | Schamper et al. ........... 424/66 |
| 4,704,421 A | 11/1987 | Teskin ....................... 524/287 |
| 4,739,017 A | 4/1988 | Tabor et al. ................ 525/300 |
| 4,743,444 A | 5/1988 | McCall ........................ 424/65 |
| 4,778,837 A | 10/1988 | Waterman et al. ............ 524/89 |
| 4,801,637 A | 1/1989 | McCullough et al. ....... 524/287 |
| 4,808,650 A | 2/1989 | Titus et al. ................. 524/108 |
| 4,816,261 A | 3/1989 | Luebbe et al. ................ 424/65 |
| 4,829,114 A | 5/1989 | Trotoir et al. ............... 524/243 |
| 4,902,807 A | 2/1990 | Kobayashi et al. ......... 549/364 |
| 5,013,778 A | 5/1991 | Bath et al. .................. 524/173 |
| 5,049,605 A | 9/1991 | Rekers ....................... 524/108 |
| 5,106,999 A | 4/1992 | Gardik et al. ............... 549/364 |
| 5,135,975 A | 8/1992 | Rekers et al. .............. 524/108 |
| 5,138,099 A | 8/1992 | Lang .......................... 568/435 |
| 5,470,898 A | 11/1995 | Syed ........................... 524/84 |
| 5,491,187 A | 2/1996 | Ward et al. ................. 524/159 |
| 5,609,855 A | 3/1997 | Oh et al. ....................... 424/65 |
| 5,696,186 A | 12/1997 | Videau ......................... 524/48 |
| 5,731,474 A | 3/1998 | Scrivens et al. ............ 330/253 |
| 5,922,793 A | 7/1999 | Amos et al. ................ 524/159 |
| 5,929,146 A | 7/1999 | Amos et al. .................. 524/89 |
| 6,096,811 A | 8/2000 | Amos et al. .................. 524/89 |
| 6,187,842 B1 | 2/2001 | Kobayashi et al. ......... 549/364 |
| 6,300,525 B1 | 10/2001 | Anderson et al. ........... 568/428 |

FOREIGN PATENT DOCUMENTS

| | | | |
|---|---|---|---|
| DE | 1 544 851 | 5/1970 | .......... C08F/29/02 |
| DE | 1 694 914 B | 3/1972 | .......... C08F/29/02 |
| EP | 0267 695 | 5/1988 | ............ C08K/5/00 |
| EP | 0336 573 | 3/1989 | ............ C08K/5/00 |
| EP | 0 421 329 | 10/1990 | |
| FR | 2 075 549 | 9/1971 | .......... C08F/45/00 |
| FR | 2 656 620 | 7/1991 | .......... C08L/23/02 |
| GB | 2 290 296 | 12/1995 | ......... C08K/5/3412 |
| JP | 53-40760 | 4/1978 | ................ 548/435 |
| JP | 57-18682 | 1/1982 | |
| JP | 58-160343 | 9/1983 | .......... C08L/67/20 |

(Continued)

OTHER PUBLICATIONS

Patent Abstracts of Japan; Publication No.: 01062377; Publication Date: Aug. 3, 1989; Fluorinated dibenzylidene polyhydric alcohol derivative, nonaqueous gelatinizing agent containing said derivative and cosmetic using said derivative; Foreign text.

(Continued)

*Primary Examiner*—D. Margaret Seaman
*Assistant Examiner*—Raymond Covington
(74) *Attorney, Agent, or Firm*—Terry T. Moyer; John E. Vick, Jr.

(57) ABSTRACT

Plastic additives which are useful as nucleating agents and which are especially useful for improving the optical properties of polymeric materials are provided. More particularly, this invention relates to certain alkyl (or alkoxy) substituted fluoro-benzylidene sorbitol acetals and polymer compositions thereof which may be utilized within, as merely examples, food or cosmetic containers and packaging. These inventive fluorinated and alkylated benzylidene sorbitol acetals are also useful as gelling agents for water and organic solvents, particularly those used in the preparation of antiperspirant gel sticks.

14 Claims, No Drawings

FOREIGN PATENT DOCUMENTS

| JP | 60-13837 | 1/1985 | |
| JP | 61-17834 | 5/1986 | |
| JP | 01-180514 | 7/1989 | ............ G02C/7/02 |
| JP | 03-076815 A | 4/1991 | ............ D01F/8/06 |
| JP | 05-139460 | 6/1993 | ........... B65D/77/00 |
| JP | 07-173342 | 7/1995 | ........... C08L/23/10 |
| WO | 92/19221 | 11/1992 | |

OTHER PUBLICATIONS

PCT International Seach Report; Applicant's File No.: WO5198; International Application No.: PCT/US01/26281; International Filing Date: Aug. 23, 2001.

PCT International Preliminary Examination Report; Applicant's File No.: WO5198; International Application No.: PCT/US01/26281; International Filing Date: Aug. 23, 2001.

H.N. Beck, "Heterogeneous Nucleating Agents of Polypropylene Crystallization", Journal of Applied Polymer Science, vol. 11, pp. 673–685, 1967.

Overman et al., "An Annual Publication of Satisfactory Methods for the P reparation of O rganic Chemicals." Organic Synthesis, vol. 71, pp. 48–55, 1993.

Snider et al., "Mn(III)–Based Oxidative Free Radical Cyclization of Unsaturated Ketones," Journal of Organic Chemistry, vol. 60, pp. 5376–5377, 1995.

Fillon et al., "Self–Nucleation and Recrystallization of Isotactic Polypropylene (alpha Phase) Investigated by Differential Scanning Calorimetry," Journal of Polymer Science: Part B: Polymer Physics, vol. 31, pp. 1383–1393, 1993.

Fillon et al., "Self–Nucleation and Enhanced Nucleation of Polymers. Definition of a Convenient Calorimetric "Efficiency Scale" and Evaluation of Nucleating Additives in Isotactic Polypropylene (alpha phase)," Journal of Polymer Science: Part B: Polymer Physics vol. 31, pp. 1395–1504, 1993.

POLYMER ADDITIVE COMPOSITIONS AND ARTICLES COMPRISING NOVEL FLUORINATED AND ALKYLATED ALDITOL DERIVATIVES

CROSS REFERENCE TO RELATED APPLICATIONS

This application is a divisional of application Ser. No. 09/816,965, filed on Mar. 23, 2001 now abandoned, which is a continuation-in-part of application Ser. No. 09/653,935, filed on Sep. 1, 2000, now U.S. Pat. No. 6,300,525. These parent applications are herein entirely incorporated by reference.

FIELD OF THE INVENTION

This invention relates to plastic additives which are useful as nucleating agents and which are especially useful for improving the optical properties of polymeric materials. More particularly, this invention relates to certain alkyl (or alkoxy) substituted fluoro-benzylidene sorbitol acetals and polymer compositions thereof which may be utilized within, as merely examples, food or cosmetic containers and packaging. These inventive fluorinated and alkylated benzylidene sorbitol acetals are also useful as gelling agents for water and organic solvents, particularly those used in the preparation of antiperspirant gel sticks.

BACKGROUND OF THE PRIOR ART

All U.S. Patents cited below are herein entirely incorporated by reference.

Numerous attempts have been made to improve the clarity and physical properties of polyolefins through the incorporation of certain kinds of additives. Certain applications require good clarity or transparency characteristics. These include certain types of plastic plates, sheets, films, containers, and syringes that need to exhibit clarity primarily to facilitate identification of articles, etc., stored, wrapped, and/or covered therewith. Such commercially available plastic additives fall into two categories termed "melt sensitive" and "melt insensitive". Melt sensitive additives possess melting points below or near the normal processing temperatures of polyolefin-based resins and include dibenzylidene sorbitol (DBS) systems. Melt insensitive additives do not melt at normal processing temperatures and include sodium benzoate and salts of organic phosphates as examples.

U.S. Pat. No. 4,016,118 to Hamada, et al. teaches that a polyolefin plastic composition containing 0.1% to 0.7% dibenzylidene sorbitol (DBS) as an additive will show improved transparency and reduced molding shrinkage over compositions containing a substituted benzoic acid salt. Additional advancements in sorbitol-based clarification technology have been driven by the need for improved transparency, reduction of plate-out during processing, and improved organoleptic properties (e.g., odor, taste, etc.). In order to overcome these deficiencies, many derivatives of DBS in which the aromatic rings are substituted with various groups have been proposed.

Mahaffey, in U.S. Pat. No. 4,371,645 discloses a series of dibenzylidene sorbitols having the general formula:

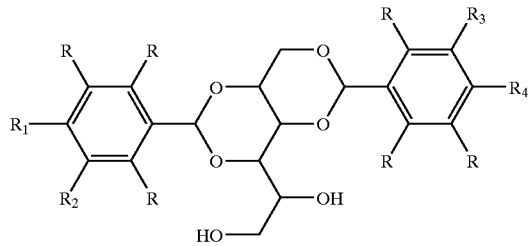

wherein R, $R_1$, $R_2$, $R_3$, and $R_4$, are selected from hydrogen, lower alkyl, hydroxy, methoxy, mono- and di-alkylamino, amino, nitro, and halogen, with the proviso that at least one of $R_1$, $R_2$, $R_3$, and $R_4$ is chlorine or bromine. Effective concentrations of the disclosed substituted DBS derivatives range from 0.01 to about 2 percent of the total composition by weight. Further improvements in transparency characteristics are disclosed by Titus, et al. in U.S. Pat. No. 4,808,650. In this patent mono and disubstituted DBS derivatives having the formula:

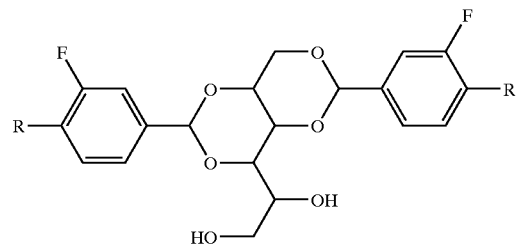

in which R may be hydrogen or fluorine provide improved clarity applications in polyolefins. Rekers, in U.S. Pat. No. 5,049,605 discloses a series of dibenzylidene sorbitols having the general formula:

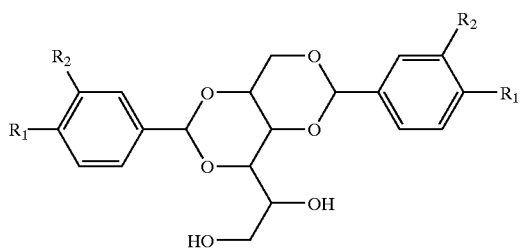

in which $R_1$ and $R_2$ are independently selected from lower alkyl groups containing 1–4 carbons which together form a carbocyclic ring containing up to 5 carbon atoms. Also disclosed are polyolefin plastics containing the above group of dibenzylidene sorbitols. Videau, in U.S. Pat. No. 5,696,186 discloses substituted DBS derivatives with an alkyl group (methyl, ethyl, or the like) or halogen (fluorine, chlorine, or the like) on the benzene rings for use as nucleation/clarification agents in polyolefins.

Dibenzylidene sorbitol (DBS) is a well known gelling agent for a variety solvent systems as disclosed in U.S. Pat. No. 4,154,816, Roehl et al.; U.S. Pat. No. 4,816,261, Luebbe et al.; and U.S. Pat. No. 4,743,444 to McCall. U.S. Pat. No. 5,609,855 to Oh et al. and PCT Patent Application WO/92/19221 to Juneja et al.; disclose that di(meta-fluorobenzylidene) sorbitol and di(meta-chlorobenzylidene) sorbitol are extremely useful as gelling agents in the preparation of antiperspirant gel sticks. These two respective DBS systems form effective hard gels and show improved gel stability in the acidic environment of antiperspirant formulations.

DETAILED DESCRIPTION OF THE INVENTION

According to the present invention, a polyolefin plastic composition having improved transparency is provided which comprises a polymer selected from aliphatic polyolefins and copolymers containing at least one aliphatic olefin and one or more ethylenically unsaturated comonomers and at least one di-acetal of an alditol (such as sorbitol, xylitol, and ribitol), said di-acetal of the alditol having the structure:

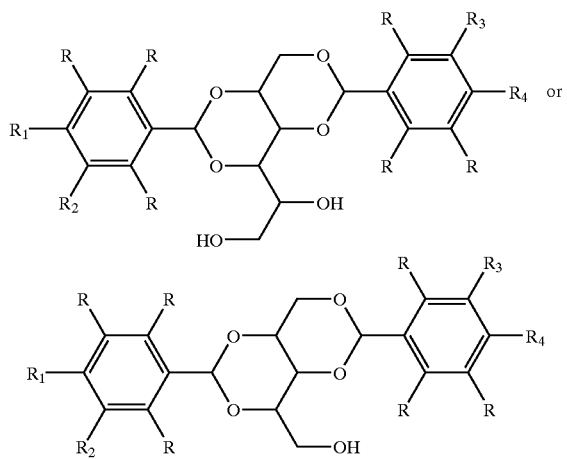

wherein R is independently selected from hydrogen, lower alkyl groups containing 1–4 carbon atoms, lower alkoxy groups, and fluorine; $R_1$, $R_2$, $R_3$, and $R_4$ are selected from lower alkyl groups containing 1–4 carbon atoms, lower alkoxy groups, chlorine, and fluorine; with the proviso that one and only one of $R_1$ and $R_2$ is fluorine and one and only one of $R_3$ and $R_4$ is fluorine.

This invention also encompasses such specific compounds themselves, in their broadest sense defined as benzylidene alditol acetals comprising at least one substituted benzylidene component wherein said at least one substituted benzylidene component possesses at least one fluorine pendant group and at least one other pendant group, wherein said at least one other pendant group is not hydrogen, and wherein if said at least one other pendant group is fluorine, at least one other non-hydrogen pendant group is present on said benzylidene component. Furthermore, a composition of the same type of thermoplastic comprising at least one mono-acetal alditol of the structure:

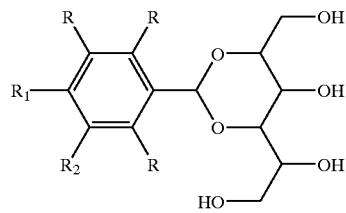

wherein R is independently selected from hydrogen, lower alkyl groups containing 1–4 carbon atoms, lower alkoxy groups, chlorine, and fluorine; $R_1$ and $R_2$ are selected from lower alkyl groups containing 1–4 carbon atoms, lower alkoxy groups, chlorine, and fluorine; with the proviso that one and only one of $R_1$ and $R_2$ is fluorine. Such monoacetal compounds are also encompassed within this invention.

It should be appreciated with regard to the structural formula set forth above that while only the 1,3:2,4 isomer is represented, this structure is provided for convenience only and the invention is not limited to only isomers of the 1,3:2,4 type, but may include any and all other isomers as well so long as the compound contains two aldehyde substitutents on the alditol moiety.

The diacetals and monoacetals of the present invention are condensation products of alditol, such as sorbitol or xylitol, and a fluoro-alkyl substituted benzaldehyde. Examples of suitable substituted benzaldehydes include 4-fluoro-3-methylbenzaldehyde, 3-fluoro-4-methylbenzaldehyde, 4-fluoro-2,3-dimethylbenzaldehyde, 3-fluoro-2,4-dimethylbenzaldehyde, 2,4-difluoro-3-methylbenzaldehyde, 4-fluoro-3,5-dimethylbenzaldehyde, and 3-fluoro-4-methoxybenzaldehyde. Preferred di-acetals of the present invention include bis(4-fluoro-3-methylbenzylidene) sorbitol and bis(3-fluoro-4-methylbenzylidene) sorbitol.

The compositions of the present invention also include solvent gels containing 0.2% to 10% of the above di-acetals as a gelling agent. Solvents useful herein include, as merely examples, lower monohydric alcohols, polyhydric alcohols, and mixtures thereof. Water may also be included as a portion of the solvent. However, the solvent will generally comprise water at levels no greater than 5% by weight of the final composition. Examples of solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol, monomethyl ether, diethylene glycol, monoethylether, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivatives). Examples of such compounds are butyl ether derivatives of polypropylene polyethylene glycol copolymers, such as PPG-5-buteth-7.

These solvents are fully described, for example, in U.S. Pat. No. 4,518,582 to Schamper et al. and European Published Application 107,330 to Luebbe et al. incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, dipropylene glycol, tripropylene glycol, triethylene glycol, hexylene gylcol, and mixtures thereof.

Other organic solvents useful herein include aromatics, halogenated aromatics, nitrated aromatics, ketones, amines, nitriles, esters, aldehydes, and mixtures thereof. Examples of solvents which may be utilized in the present invention include xylenes (o, m, and p-substituted), 2-chlorotoluene, fluorobenzene, nitrobenzene, benzonitrile, dimethylsulfoxide (DMSO), N,N-dimethylformamide (DMF), and 1-methyl-2-pyrrolidinone (NMP).

The di-acetals and monoacetals of the present invention may be prepared by a variety of techniques, some of which are known in the art. Generally, such procedures employ the reaction of one mole of D-sorbitol with about 2 moles of aldehyde (for diacetals), with 1 mole of aldehyde for monoacetals, in the presence of an acid catalyst. The temperature employed in the reaction will vary widely depending upon the characteristics, such as melting point, of the aldehyde or aldehydes employed as a starting material in the reaction. The reaction medium may be an aqueous medium or a non-aqueous medium. One very advantageous method that can be employed to prepare di-acetals of the invention is described in U.S. Pat. No. 3,721,682, to Murai et al. (New Japan Chemical Company Limited), the disclosure of which is hereby incorporated herein by reference. While the disclosure of the patent is limited to benzylidene sorbitols, it has been found that the di-acetals of the present invention may also be conveniently prepared by the method described therein. Additional methods for preparing DBS systems can be found in U.S. Pat. No. 5,731,474 to Scrivens et al., U.S. Pat. No. 4,902,807 to Kobayashi et al. which discloses DBS having an alkyl group or halogen for use as clarifying agents, and U.S. Pat. No. 5,106,999 to Gardlik et al. which discloses the preparation of di(meta-fluorobenzylidene) sorbitol, di(meta-chlorobenzylidene)sorbitol, and di(meta-bromobenzylidene)sorbitol.

The inventive sorbitol di-acetals and monoacetals prepared by the above techniques may contain minor impurities (triacetals, for example). Although it may not always be necessary to remove these impurities (particularly if they are present in very low proportions) prior to incorporation of the di-acetal or monoacetal into the target polyolefin, it may be desirable to do so and such purification may serve to enhance the transparency of the resin produced thereby. Purification of the di-acetal may be accomplished, for instance, by removal of the tri-acetal impurities by the extraction thereof with a relatively non-polar solvent. By removal of the impurities, the product may be purified so that the amount of di-acetal in the additive composition contains at least about 90 percent and even up to 95 percent di-acetal or more.

The proportion of di-acetal or monoacetal in the composition of this invention is an amount sufficient to improve the transparency of the composition, generally from about 0.01 to about 2 percent by weight, preferably about 0.1 to about 1 percent by weight, based upon the total weight of the composition may be provided. When the content of the di-acetal is less than about 0.01 percent by weight, the resulting composition may not be sufficiently improved in respect to transparency characteristics. When the content of di-acetal or monoacetal is increased beyond about 2 percent by weight, no additional advantage can be observed.

The polyolefin polymers of the present invention may include aliphatic polyolefins and copolymers made from at least one aliphatic olefin and one or more ethylenically unsaturated comonomers. Generally, the comonomers, if present, constitute a minor amount, e.g., about 10 percent or less or even about 5 percent or less, of the entire polyolefin, based upon the total weight of the polyolefin. Such comonomers may serve to assist in clarity improvement of the polyolefin, or they may function to improve other properties of the polymer. Examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as polyethylene, linear low density polyethylene, polypropylene, crystalline ethylenepropylene copolymer, poly(1-butene), 1-hexene, 1-octene, vinyl cyclohexane, and polymethylpentene. The polyolefins of the present invention may be described as basically linear, regular polymers that may optionally contain side chains such as are found, for instance, in conventional, low density polyethylene.

Other polymers that may benefit from the nucleation and clarification properties of the sorbitol acetals of the present invention include polyethylene terephthalate, polybutylene terephthalate, and polyamides, among others.

The olefin polymer or copolymer used in the composition of the present invention is crystalline, and the diffraction of light caused by micro crystals contained in it is considered to be responsible for the deterioration of the transparency of the polymer. It is thought that the di-acetal functions in the composition to reduce the size of the microcrystals thereby improving the transparency of the polymer.

The composition of the present invention can be obtained by adding a specific amount of the di-acetal or monoacetal directly to the olefin polymer or copolymer, and merely mixing them by an suitable means. Alternatively, a concentrate containing as much as about 20 percent by weight of the di-acetal in a polyolefin masterbatch may be prepared and be subsequently mixed with the resin. Furthermore, the inventive alditol derivatives (and other additives) may be present in any type of standard polyolefin additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

Other additives such as a transparent coloring agent or plasticizers (e.g., dioctyl phthalate, dibutyl phthalate, dioctyl sebacate, mineral oil, or dioctyl adipate), can be added to the composition of the present invention so long as they do not adversely affect the improvement of transparency of the product. It has been found that plasticizers such as those exemplified above may in fact aid in the improvement of the transparency by the di-acetal.

With regard to other additives it may also be desirable to employ the di-acetals or monoacetals disclosed above in combination with other conventional additives having known transparency improving effects such as, for instance, para-t-butylbenzoic acid, its salts, low molecular weight waxy polypropylene and the like. It may even be desirable to provide the particular di-acetals or monoacetals of the present invention in the polyolefin composition in combination with the previously described dibenzylidene sorbitol additive disclosed in U.S. Pat. No. 4,016,118 to Hamada et al. In such applications, generally at least about 10 percent, preferably about 25 percent, or even about 50 percent or more of the clarity improving component will be the diacetals of the present invention, with the remainder being comprised of other known clarifying agents, plasticizers, etc.

The compositions of the present invention may be obtained by adding the fluorinated and alkylated benzylidene sorbitol acetal to the polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

Other additives may also be used in the composition of the present invention, provided they do not interfere with the primary benefits of the invention. It may even be advantageous to premix these additives or similar structures with the nucleating agent in order to reduce its melting point and thereby enhance dispersion and distribution during melt processing. Of particular interest is the incorporation of the inventive symmetrical compound or compounds with, without limitation to any specific additive nucleators or clarifiers, selected amounts, for example bis(3,4-dimethylbenzylidene) sorbitol (hereinafter DMDBS), bis(3,4-dichlorobenzylidene) sorbitol, bis(3,4-difluorobenzylidene)sorbitol, bis(3-chloro-4-fluorobenzylidene) sorbitol, and bis(4-chloro-3-fluorobenzylidene)sorbitol. As noted below, such a combination provides unexpected haze benefits within target polyolefin (e.g., polypropylene) plastic articles. Such additives are well known to those skilled in the art, and include plasticizers, lubricants, catalyst neutralizers, antioxidants, light stabilizers, colorants, other nucleating agents, and the like. Some of these additives may provide further beneficial property enhancements, including improved aesthetics, easier processing, and improved stability to processing or end use conditions.

In particular, it is contemplated that certain organoleptic improvement additives be added for the purpose of reducing the migration of degraded benzaldehydes from reaching the surface of the desired article. The term "organoleptic improvement additive" is intended to encompass such compounds and formulations as antioxidants (to prevent degradation of both the polyolefin and possibly the target alditol derivatives present within such polyolefin), acid neutralizers (to prevent the ability of appreciable amounts of residual acids from attacking the alditol derivatives), and benzaldehyde scavengers (such as hydrazides, hydrazines, and the like, to prevent the migration of foul tasting and smelling benzaldehydes to the target polyolefin surface). Such compounds and formulations can be added in any amounts in order to provide such organoleptic improvements as needed. However, the amounts should not appreciably affect the haze results for the target polyolefin itself. Thus, lower amounts on the order of from about 20 ppm to about 2,000 ppm of the total polyolefin component are desired.

The compositions of the present invention are suitable as additives to improve the clarity of packaging materials and container materials for cosmetics, food-stuffs, and the like, because they give film, sheet, and other fabricated articles having excellent transparency and physical properties.

Preferred Embodiments of the Invention

The following examples further illustrate the present invention but are not to be construed as limiting the invention as defined in the claims appended hereto. All parts and percents given in these examples are by weight unless otherwise indicated.

DBS Formation

EXAMPLE 1

Preparation of Bis(4-fluoro-3-methylbenzylidene) sorbitol

A one liter four-necked cylindrical shaped reaction flask equipped with a Dean-Stark trap, condenser, thermometer, nitrogen inlet, and a mechanical stirrer was charged with 40.55 g of sorbitol (0.2226 mole), 600 mL of cyclohexane, 61.50 g of 4-fluoro-3-methylbenzaldehyde (0.4452 moles), 2.90 g of p-toluenesulfonic acid, 2.4 mL of water, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake was washed thoroughly with water and cyclohexane, dried in a vacuum oven at 110° C. to give 74.20 g of Bis(4-fluoro-3-methylbenzylidene)sorbitol (as determined through Infrared Spectroscopy, Gas Chromatography/Mass Spectrometry, $^1$H NMR, and $C^{13}$ NMR, all collectively hereinafter referred to as "standard analyses"). The purity was about 95% as determined by gas chromatography (GC). The melting point was determined to be [by Differential Scanning Calorimetry (DSC) @ 20° C./min] about 237.8° C.

EXAMPLE 2

Preparation of Bis(3-fluoro-4-methylbenzylidene )sorbitol

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 600 mL of cyclohexane, 63.70 g of 3-fluoro-4-methylbenzaldehyde (0.4611 moles), 3.00 g of p-toluenesulfonic acid, 2.5 mL of water, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake was washed thoroughly with water and cyclohexane, dried in a vacuum oven at 110° C. to give 85.18 g of Bis(3-fluoro-4-methylbenzylidene)sorbitol (as determined through standard analyses). The purity was about 95% as determined by GC. The melting point was determined to be (DSC @ 20° C./min) about 278.8° C.

EXAMPLE 3

Preparation of Bis(4-fluoro-3-methylbenzylidene) xylitol

A one liter four-necked cylindrical shaped reaction flask equipped with a Dean-Stark trap, condenser, thermometer, nitrogen inlet, and a mechanical stirrer was charged with 35.08 g of xylitol (0.2306 mole), 600 mL of cyclohexane, 63.70 g of 4-fluoro-3-methylbenzaldehyde (0.4611 moles), 3.00 g of p-toluenesulfonic acid, 2.5 mL of water, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake was washed thoroughly with water and cyclohexane, dried in a vacuum oven at 110° C. to give 69.46 g of Bis(4-fluoro-3-methylbenzylidene)xylitol (as determined through standard analyses). The purity was about 95% as determined by GC. The melting point was determined to be (DSC @ 20° C./min) about 222.9° C.

EXAMPLE 4

Preparation of 2,4-Mono(4-fluoro-3-methylbenzylidene)sorbitol

A two liter cylindrical shaped reaction flask equipped with a mechanical stirrer was charged with 237.37 g of sorbitol (1.303 mole), 250 mL of water, 22.50 g of 4-fluoro-3-metbylbenzaldehyde (0.1629 moles), 40 mL of concentrated HCl, and 0.20 g of dodecylbenzene sulfonate. The reaction mixture was then stirred for 14 h at 25° C. After neutralization with 56.0 g of KOH, crude 2,4-Mono(4-fluoro-3-methylbenzylidene)sorbitol was filtered and collected. The crude product was recrystallized from water several times to give 3.31 g of 2,4-mono(4-fluoro-3-methylbenzylidene)sorbitol having the structure of:

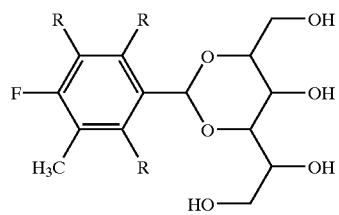

(through standard analyses). The purity was about 98% as judged by GC. The melting point was measured (DSC @ 20° C./min) to be about 178.0° C.

EXAMPLE 5

Preparation of Bis(4-chloro-3-fluorobenzylidene) sorbitol

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 600 mL of cyclohexane, 73.11 g of 4-chloro-3-fluorobenzaldehyde (0.4611 moles), 3.00 g of p-toluenesulfonic acid, 2.5 mL of water, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 93.02 g of Bis(4-chloro-3-fluorobenzylidene)sorbitol (as determined through standard analyses). The purity was about 95% as judged by GC. The melting point was measured (DSC @ 20° C./min) to be about 262.0° C.

EXAMPLE 6

Preparation of Bis(3-chloro-4-fluorobenzylidene) sorbitol

A one liter four-necked cylindrical shaped reaction flask equipped with a Dean-Stark trap, condenser, thermometer, nitrogen inlet, and a mechanical stirrer was charged with 34.30 g of sorbitol (0.1883 mole), 600 mL of cyclohexane, 59.70 g of 3-chloro-4-fluorobenzaldehyde (0.3765 moles), 2.50 g of p-toluenesulfonic acid, 2.1 mL of water, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 39.13 g of Bis(3-chloro-4-fluorobenzylidene)sorbitol (as determined through standard analyses). The purity was about 95% as judged by GC. The compound showed melting transitions (DSC @ 20° C./min) at 204.8 and 220.0° C.

Polyolefin Formation and Testing

Thermoplastic compositions (plaques) and certain gels were produced comprising a the additives from the EXAMPLEs above and sample random copolymer polypropylene (RCP) resins, polypropylene homopolymers (HP), Impact Copolymer (ICP), and Linear Low Density Polyethylene (LLDPE), produced dry blended in a Welex mixer at ~2000 rpm, extruded through a single screw extruder at 400–450° F., and pelletized. Accordingly, one kilogram batches of target polypropylene were produced in accordance with the following table:

| RANDOM COPOLYMER POLYPROPYLENE COMPOSITION TABLE | |
| --- | --- |
| Component | Amount |
| Polypropylene random copolymer flake (3% ethylene) (MF = 12) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Diacetal (and diacetal compositions) | as noted |

The base resin (random copolymer, hereinafter "RCP") and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder molder was set at a temperature anywhere between 190 and 260° C., with a range of 190 to 240° C. preferred, most preferably from about 200 to 230° C. (for the Tables below, the standard temperature was 220; a # denotes a temperature 210, a ^ denotes a temperature of 200, and a @ denotes a temperature of 230). The plaques had dimensions of about 51 mm×76 mm×1.27 mm, and were made in a mold having a mirror finish. The mold cooling circulating water was controlled at a temperature of about 25° C.

The same basic procedures were followed for the production of plaques of HP and LLDPE plastics but with the following compositions:

| HOMOPOLYMER POLYPROPYLENE COMPOSITION TABLE | |
| --- | --- |
| Component | Amount |
| Polypropylene homopolymer (MFI = 12) (Montell 630) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Diacetal (and diacetal compositions) | as noted |

| LINEAR LOW DENSITY POLYETHYLENE COMPOSITION TABLE | |
| --- | --- |
| Component | Amount |
| Dowlex ® 2517 Linear Low Density Polyethylene (with Antioxidants and Acid scavengers already supplied) | 1000 g |
| Sodium Stearate | 500 ppm |
| Inventive Diacetal (and diacetal compositions) | as noted |

The haze values were measured by ASTM Standard Test Method D1003-61 "Standard Test Method for Haze and Luminous Transmittance of Transparent Plastics" using a BYK Gardner XL-211 Hazemeter. Nucleation capabilities were measured as polymer recrystallization temperatures (which indicate the rate of polymer formation provided by the presence of the nucleating additive) by melting the target plaques, cooling the plaques at a rate of about 20° C./minute, and recording the temperature at which polymer re-formation occurs. Control plaques without alditol additives as well as 3,4-dimethyldibenzylidene sorbitol (3,4-DMDBS) were produced for comparative purposes for some or all of the above-noted measurements. Plaques of various thicknesses (50 mil, 100 mil, and 3 mm) were then prepared by injection molding at 400–430° F. The haze values were measured by ASTM Standard Test Method D1003-61 "Haze and luminous transmittance of transparent plastics" using a Gardner Hazemeter. Control plaques without alditol additives as well as 3,4-dimethyldibenzylidene sorbitol (3,4-DMDBS), 3,4-dimethyldibenzylidene xylitol (3,4-DMDBS), dibenzylidene sorbitol (DBS) alone, and NA-11 (a polyolefin nucleator available from Asahi Denka Co.) containing plaques, as noted below within the examples, were produced for comparative purposes for some or all of the above-noted measurements. An asterisk (*) denotes no measurements were taken.

TABLE 1

| Ex. No. | Additive - from Example # above | Conc. (%) | Haze (%) | Resin Grade | Part Thick. (mil) | Polym. Recryst. Temp. |
| --- | --- | --- | --- | --- | --- | --- |
| 4 | Control | — | 60.9 | RCP | 50 | 94.6 |
| 5 | 2 | .15 | 16.9 | RCP | 50 | * |
| 6 | 2 | .25 | 7.8 | RCP | 50 | 111.8 |
| 7 | 2 | .35 | 7.2 | RCP | 50 | 112.2 |
| 8 | 2 | .50 | 7.0 | RCP | 50 | * |

TABLE 2

| Ex. No. | Additive - from Example # above | Conc. (%) | Haze (%) | Resin Grade | Part Thick. (mil) | Polym. Recryst. Temp. |
| --- | --- | --- | --- | --- | --- | --- |
| 9 | Control (#) | — | 59.8 | RCP | 50 | 94.3 |
| 10 | 1 (#) | .16 | 19.2 | RCP | 50 | * |
| 11 | 1 (#) | .24 | 8.6 | RCP | 50 | * |
| 12 | 1 (#) | .30 | 7.1 | RCP | 50 | 114.1 |
| 13 | 1 (#) | .40 | 6.8 | RCP | 50 | 114.3 |

TABLE 3

| Ex. No. | Additive - from Example # above | Conc. (%) | Haze (%) | Resin Grade | Part Thick. (mil) | Polym. Recryst. Temp. |
| --- | --- | --- | --- | --- | --- | --- |
| 14 | Control (^) | — | 61.3 | RCP | 50 | 95.1 |
| 15 | 3 (^) | .15 | 55.6 | RCP | 50 | * |
| 16 | 3 (^) | .25 | 49.1 | RCP | 50 | * |
| 17 | 3 (^) | .35 | 45.7 | RCP | 50 | * |
| 18 | 3 (^) | .50 | 38.0 | RCP | 50 | 108.1 |
| 19 | 3,4-DMDBX (^) | .50 | 25.0 | RCP | 50 | 109.4 |

TABLE 4

| Ex. No. | Additive - from Example # above | Conc. (%) | Haze (%) | Resin Grade | Part Thick. (mil) |
| --- | --- | --- | --- | --- | --- |
| 20 | Control | — | 90.7 | RCP | 100 |
| 21 | 1 | .25 | 30.0 | RCP | 100 |
| 22 | 1 | .35 | 28.4 | RCP | 100 |
| 23 | 1 | .45 | 27.2 | RCP | 100 |
| 24 | 5 (#) | .12 | 26.1 | RCP | 50 |
| 25 | 5 (#) | .16 | 12.4 | RCP | 50 |
| 26 | 5 (#) | .24 | 8.0 | RCP | 50 |
| 27 | 5 (#) | .30 | 7.6 | RCP | 50 |
| 28 | 5 (#) | .40 | 7.3 | RCP | 50 |
| 29 | 6 | .25 | 17.0 | RCP | 50 |
| 30 | 6 | .35 | 10.4 | RCP | 50 |
| 31 | 6 | .50 | 8.3 | RCP | 50 |

TABLE 5

| Ex. No. | Additive - from Example # above | Conc. (%) | Haze (%) | Resin Grade | Part Thick. (mil) | Polym. Recryst. Temp. |
| --- | --- | --- | --- | --- | --- | --- |
| 32 | None (@) | — | 78.1 | HP | 50 | 107.9 |
| 33 | 1 (@) | .25 | 19.4 | HP | 50 | 121.9 |
| 34 | 1 (@) | .35 | 11.5 | HP | 50 | 125.3 |
| 35 | 1 (@) | .50 | 10.0 | HP | 50 | * |
| 36 | 4 (@) | .25 | 67.7 | HP | 50 | 110.3 |

TABLE 6

| Ex. No. | Additive - from Example # above | Conc. (%) | Resin Grade | Part Thick (mm) | Polym. Recryst. Temp. | Flex Mod. (MPa) |
| --- | --- | --- | --- | --- | --- | --- |
| 37 | None (@) | — | ICP | 3.0 | 107.9 | 1005 |
| 38 | 1 (@) | .20 | ICP | 3.0 | 115.2 | 1138 |
| 39 | 1 (@) | .25 | ICP | 3.0 | 121.3 | 1179 |
| 40 | 1 (@) | .35 | ICP | 3.0 | 124.5 | 1207 |
| 41 | NA-11 | .10 | ICP | 3.0 | 122.8 | 1158 |

TABLE 7

| Ex. No. | Additive - from Example # above | Conc. (%) | Haze (%) | Resin Grade | Part Thick. (mil) | Polym. Recryst. Temp. |
| --- | --- | --- | --- | --- | --- | --- |
| 42 | None (^) | — | 93.9 | LLDPE | 50 | 99.0 |
| 43 | 1 (^) | .15 | 55.3 | LLDPE | 50 | * |
| 44 | 1 (^) | .20 | 47.1 | LLDPE | 50 | * |
| 45 | 1 (^) | .25 | 47.6 | LLDPE | 50 | 108.1 |
| 46 | 1 (^) | .15 | 51.9 | LLDPE | 50 | * |
| 47 | 1 (^) | .20 | 53.6 | LLDPE | 50 | * |
| 48 | 3,4-DMDBS (^) | .25 | 53.6 | LLDPE | 50 | 108.3 |
| 49 | DBS (^) | .15 | 63.0 | LLDPE | 50 | * |
| 50 | DBS (^) | .25 | 62.6 | LLDPE | 50 | 106.1 |

Thus, the inventive fluoro-alkyl alditol derivatives provided similar, if not better, characteristics within the target thermoplastics as compared with the control and other compositions comprising other types of clarifying and/or nucleating additives.

Gel Formation Examples

Solid gels were also produced comprising the inventive alditol derivatives through recognized, simple methods. In particular, specific organic solvents were combined with the additives in certain concentrations and mixed thoroughly. The resultant mixture was then heated to a temperature between about 170° F. (77° C.) and 300° F. (149° C.), as indicated below, under agitation for between 5 and 120 minutes. The resultant solution was then poured into a mold to produce a gel stick. The solvents listed below are not intended to be exhaustive as to the potential types which may be utilized to form gels with the inventive alditol derivatives, and thus are merely listed as preferred solvents for such purposes. The examples below were analyzed empirically and by touch to determine if a gel actually formed and the hardness properties as well as any formed gels.

TABLE 8

| Ex. No. | Solvent | Additive - from Example # above | DBS Conc. (weight %) | Gel Formation (Y/N) | Gel Character (Hard/Soft) |
|---|---|---|---|---|---|
| 51 | 1,2-Propanediol | 1 | 0.5 | Y | S |
| 52 | 1,2-Propanediol | 1 | 1 | Y | H |
| 53 | 1,2-Propanediol | 1 | 2 | Y | H |
| 54 | 1,2-Propanediol | 1 | 3 | Y | H |
| 55 | 1,2-Propanediol | 1 | 5 | Y | H |
| 56 | 1,3-Propanediol | 1 | 0.5 | N | — |
| 57 | 1,3-Propanediol | 1 | 1 | Y | S |
| 58 | 1,3-Propanediol | 1 | 2 | Y | H |
| 59 | 1,3-Propanediol | 1 | 3 | Y | H |
| 60 | 1,3-Propanediol | 1 | 5 | Y | H |
| 61 | Triethylene Glycol | 1 | 0.5 | N | — |
| 62 | Triethylene Glycol | 1 | 1 | N | — |
| 63 | Triethylene Glycol | 1 | 2 | Y | H |
| 64 | Triethylene Glycol | 1 | 3 | Y | H |
| 65 | Triethylene Glycol | 1 | 5 | Y | H |
| 66 | Poly(ethyleneglycol) | 1 | 0.5 | N | — |
| 67 | Poly(ethyleneglycol) | 1 | 1 | N | — |
| 68 | Poly(ethyleneglycol) | 1 | 2 | Y | H |
| 69 | Poly(ethyleneglycol) | 1 | 3 | Y | H |
| 70 | Poly(ethyleneglycol) | 1 | 5 | Y | H |
| 71 | 1-Butanol | 1 | 0.5 | Y | S |
| 72 | 1-Butanol | 1 | 1 | Y | S |
| 73 | 1-Butanol | 1 | 2 | Y | H |
| 74 | 1-Butanol | 1 | 3 | Y | H |
| 75 | 1-Butanol | 1 | 5 | Y | H |
| 76 | Mineral Oil | 1 | 0.5 | Y | S |
| 77 | Mineral Oil | 1 | 1 | Y | S |
| 78 | Mineral Oil | 1 | 2 | Y | S |
| 79 | Mineral Oil | 1 | 3 | Y | S |
| 80 | Mineral Oil | 1 | 5 | Y | S |
| 81 | Xylene | 1 | 0.5 | Y | S |
| 82 | Xylene | 1 | 1 | Y | S |
| 83 | Xylene | 1 | 2 | Y | S |
| 84 | Xylene | 1 | 3 | Y | S |
| 85 | Xylene | 1 | 5 | Y | S |
| 86 | 2-Chlorotoluene | 1 | 0.5 | Y | S |
| 87 | 2-Chlorotoluene | 1 | 1 | Y | S |
| 88 | 2-Chlorotoluene | 1 | 2 | Y | H |
| 89 | 2-Chlorotoluene | 1 | 3 | Y | H |
| 90 | 2-Chlorotoluene | 1 | 5 | Y | H |

TABLE 9

| Ex. No. | Solvent | Additive - from Example # above | DBS Conc. (weight %) | Gel Formation (Y/N) | Gel Character (Hard/Soft) |
|---|---|---|---|---|---|
| 91 | 1,2-Propanediol | 2 | 0.5 | Y | S |
| 92 | 1,2-Propanediol | 2 | 1 | Y | H |
| 93 | 1,2-Propanediol | 2 | 3 | Y | H |
| 94 | 1,3-Propanediol | 2 | 0.5 | N | — |
| 95 | 1,3-Propanediol | 2 | 1 | Y | H |
| 96 | 1,3-Propanediol | 2 | 3 | Y | H |
| 97 | 1-Butanol | 2 | 0.5 | Y | S |
| 98 | 1-Butanol | 2 | 1 | Y | H |
| 99 | 1-Butanol | 2 | 3 | Y | H |
| 100 | 2-Chlorotoluene | 2 | 0.5 | Y | S |
| 101 | 2-Chlorotoluene | 2 | 1 | Y | S |
| 102 | 2-Chlorotoluene | 2 | 3 | Y | S |
| 103 | Nitrobenzene | 2 | 0.5 | Y | H |
| 104 | Nitrobenzene | 2 | 1 | Y | H |
| 105 | Nitrobenzene | 2 | 3 | Y | H |
| 106 | Benzonitrile | 2 | 0.5 | Y | S |
| 107 | Beuzonitrile | 2 | 1 | Y | H |
| 108 | Benzonitrile | 2 | 3 | Y | H |

Thus, the inventive fluoro-alkyl alditol derivatives provide excellent gelling capabilities for solvents, depending on their concentration without the target solvents.

Compositions with Other Clarifiers

Formulations of the inventive compound from Example 1 above were then produced incorporating other polyolefin clarifying benzylidene derivative compounds (such as DMDBS, etc., as listed in the Table below) in various proportions. RCP propylene was compounded as noted above (with lower molder barrel temperatures of about 200° C. marked with a #) but with mixtures of such other clarifiers and the inventive compounds of Example 1 into 50 mil and 100 mil plaques. Haze measurements were taken as noted above as well. The other clarifier compounds added within the samples below are as follows:

A—MDBS
B—Bis(3,4-dichlorobenzylidene)sorbitol
C—Bis(3,4-difluorobenzylidene)sorbitol
D—Bis(3-chloro-4-fluorobenzylidene)sorbitol
E—Bis(4-chloro-3-fluorobenzylidene)sorbitol The haze results for such mixed formulations within target RCP plaques are tabulated below:

TABLE 10

Physical Mixtures Inventive DBS Compounds And Other Polyolefin Clarifiers

| Test Plaque No. | Additive (Example # from above) mixed with other clarifiers (letter from above) (plus ratio of Additive to clarifier) | Conc. (%) | Haze (%) | Resin Grade | Part Thick (mil) | Polym. Recryst. Temp. (° C.) |
|---|---|---|---|---|---|---|
| 109 | 1 plus A [50/50] | .2 | 7.3 | RCP | 50 | * |
| 110 | 1 plus A [50/50] | .25 | 6.6 | RCP | 50 | * |
| 111 | 1 plus A [50/50] | .35 | 6.3 | RCP | 50 | 112.1 |
| 112 | 1 plus A [50/50] | .5 | 6.6 | RCP | 50 | * |
| 113 | 1 plus A [50/50] | .15 | 33.5 | RCP | 100 | * |
| 114 | 1 plus A [50/50] | .2 | 22.4 | RCP | 100 | * |
| 115 | 1 plus A [50/50] | .25 | 18.8 | RCP | 100 | 112.1 |
| 116 | 1 plus A [50/50] | .35 | 22.3 | RCP | 100 | * |
| 117 | 1 plus B [50/50] # | .35 | 6.4 | RCP | 50 | * |
| 118 | 1 plus B [50/50] # | .5 | 6.6 | RCP | 50 | * |
| 119 | 1 plus C [50/50] # | .35 | 8.1 | RCP | 50 | * |

TABLE 10-continued

Physical Mixtures Inventive DBS Compounds And Other Polyolefin Clarifiers

| Test Plaque No. | Additive (Example # from above) mixed with other clarifiers (letter from above) (plus ratio of Additive to clarifier) | Conc. (%) | Haze (%) | Resin Grade | Part Thick (mil) | Polym. Recryst. Temp. (° C.) |
|---|---|---|---|---|---|---|
| 120 | 1 plus C [50/50] # | .5 | 7.7 | RCP | 50 | * |
| 121 | 1 plus D [50/50] # | .35 | 8.0 | RCP | 50 | * |
| 122 | 1 plus D [50/50] # | .5 | 6.9 | RCP | 50 | * |
| 123 | 1 plus E [50/50] # | .35 | 7.7 | RCP | 50 | * |
| 124 | 1 plus E [50/50] # | .5 | 7.0 | RCP | 50 | * |

Thus, the inventive compound also exhibited excellent haze measurements in polypropylene in the presence of another clarifying agent.

There are, of course, many alternative embodiments and modifications of the present invention which are to be included within the spirit and scope of the following claims.

What is claimed is:

1. A polyolefin additive composition comprising at least one benzylidene alditol acetal, wherein said benzylidene alditol acetal comprises at least one substituted benzylidene component having at least one fluorine pendant group and at least one other pendant group, wherein said at least one other pendant group is not hydrogen, and wherein if said at least one other pendant group is fluorine, at least one other non-hydrogen pendant group is present on said benzylidene component, and wherein said composition comprises at least one other clarifying agent.

2. The composition of claim 1 wherein said other clarifying agent is selected from at least one dibenzylidene sorbitol derivative.

3. The composition of claim 2 wherein said at least one dibenzylidene sorbitol derivative is selected from the group consisting of bis(3,4-dimethylbenzylidene)sorbitol (hereinafter DMDBS), bis(3,4-dichlorobenzylidene) sorbitol, bis(3,4-difluorobenzylidene)sorbitol, bis(3-chloro-4-fluorobenzylidene)sorbitol, and bis(4-chloro-3-fluorobenzylidene)sorbitol.

4. A polyolefin additive composition comprising at least one compound conforming to the formula of either Structure (I) or Structure (II):

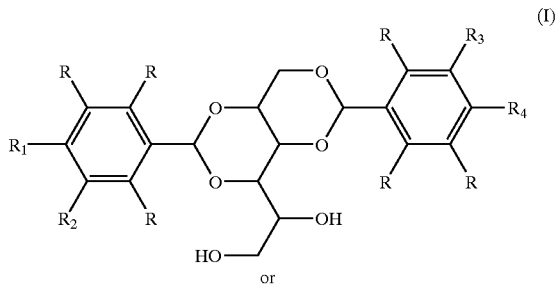

(I)

or

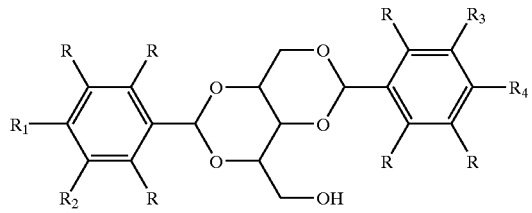

(II)

wherein R is independently selected from the group consisting of hydrogen, lower alkyl groups containing 1–4 carbon atoms, lower alkoxy groups, chlorine, and fluorine; $R_1$, $R_2$, $R_3$, and $R_4$ are independently selected from the group consisting of lower alkyl groups containing 1–4 carbon atoms, lower alkoxy groups, and fluorine; with the proviso that only one of $R_1$ and $R_2$ is fluorine, only one of $R_3$ and $R_4$ is fluorine, and wherein at least one of $R_1$, $R_2$, $R_3$, and $R_4$ is a lower alkyl group, and at least one other clarifying agent.

5. The composition of claim 4 wherein said compound is selected from the group consisting of bis(4-fluoro-3-methylbenzylidene)sorbitol; bis(3-fluoro-4-methylbenzylidene)-sorbitol; bis(4-fluoro-2,3-dimethylbenzylidene)sorbitol; bis(3-fluoro-2,4-dimethylbenzylidene)sorbitol; bis(3-fluoro-4-methoxybenzylidene)sorbitol; and bis(2,4-difluoro-3-methylbenzylidene)sorbitol.

6. The composition of claim 5 wherein said other clarifying agent is selected from at least one dibenzylidene sorbitol derivative.

7. The composition of claim 6 wherein said at least one dibenzylidene sorbitol derivative is selected from the group consisting of bis(3,4-dimethylbenzylidene)sorbitol (hereinafter DMDBS), bis(3,4-dichlorobenzylidene) sorbitol, bis(3, 4-difluorobenzylidene)sorbitol, bis(3-chloro-4-fluorobenzylidene)sorbitol, and bis(4-chloro-3-fluorobenzylidene)sorbitol.

8. A polyolefin plastic article having improved transparency and nucleation, said article comprising a polymer selected from aliphatic polyolefins and copolymers containing at least one aliphatic olefin and one or more ethylenically unsaturated aliphatic comonomers, wherein said article further comprises at least one substituted benzylidene component having at least one fluorine pendant group and at least one other pendant group, wherein said at least one other pendant group is not hydrogen, and wherein if said at least one other pendant group is fluorine, at least one other non-hydrogen pendant group is present on said benzylidene component, and at least one other clarifying agent.

9. The composition of claim 8 wherein said other clarifying agent is selected from at least one dibenzylidene sorbitol derivative.

10. The composition of claim 9 wherein said at least one dibenzylidene sorbitol derivative is selected from the group consisting of bis(3,4-dimethylbenzylidene)sorbitol (hereinafter DMDBS), bis(3,4-dichlorobenzylidene) sorbitol, bis(3, 4-difluorobenzylidene)sorbitol, bis(3-chloro-4-fluorobenzylidene)sorbitol, and bis(4-chloro-3-fluorobenzylidene)sorbitol.

11. A polyolefin plastic article having improved transparency and nucleation, said article comprising a polymer selected from aliphatic polyolefins and copolymers containing at least one aliphatic olefin and one or more ethylenically unsaturated aliphatic comonomers, wherein said article further comprises at least one benzylidene alditol acetal compound conforming to the structure of either (I) or (II)

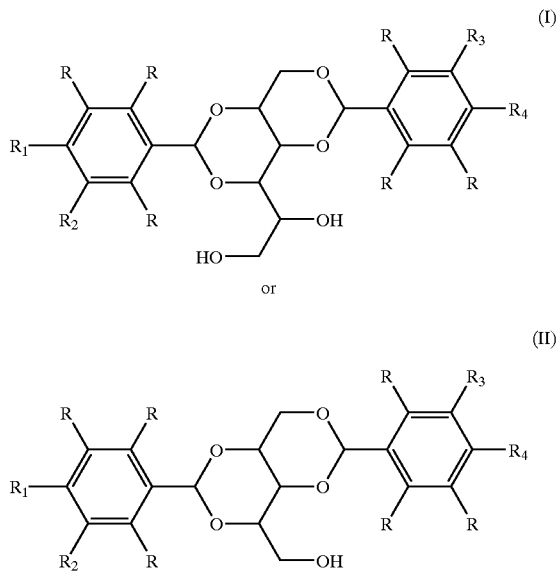

wherein R is selected from hydrogen, lower alkyl groups containing 1–4 carbon atoms, lower alkoxy groups, and fluorine; $R_1$, $R_2$, $R_3$, and $R_4$ are selected from lower alkyl groups containing 1–4 carbon atoms, lower alkoxy groups, and fluorine; with the proviso that only one of $R_1$ and $R_2$ is fluorine, only one of $R_3$ and $R_4$ is fluorine, and wherein at least one of $R_1$, $R_2$, $R_3$, and $R_4$ is a lower alkyl group, wherein said polyolefin also comprises at least one other clarifying agent.

12. The composition of claim 11, wherein said di-acetal is selected from bis(4-fluoro-3-methylbenzylidene)sorbitol; bis(3-fluoro-4-methylbenzylidene)-sorbitol; bis(4-fluoro-2,3-dimethylbenzylidene)sorbitol; bis(3-fluoro-2,4-dimethylbenzylidene)sorbitol; bis(3-fluoro-4-methoxy-benzylidene)sorbitol; and bis(2,4-difluoro-3-methylbenzylidene)sorbitol.

13. The composition of claim 12 wherein said other clarifying agent is selected from at least one dibenzylidene sorbitol derivative.

14. The composition of claim 13 wherein said at least one dibenzylidene sorbitol derivative is selected from the group consisting of bis(3,4-dimethylbenzylidene)sorbitol (hereinafter DMDBS), bis(3,4-dichlorobenzylidene)sorbitol, bis(3,4-difluorobenzylidene)sorbitol, bis(3-chloro-4-fluorobenzylidene)sorbitol, and bis(4-chloro-3-fluorobenzylidene)sorbitol.

* * * * *